(12) United States Patent
Menon et al.

(10) Patent No.: US 9,839,734 B1
(45) Date of Patent: Dec. 12, 2017

(54) AORTIC PUMP DEVICES AND METHODS

(71) Applicant: Berlin Heart GmbH, Berlin (DE)

(72) Inventors: Ares K. Menon, Berlin (DE); Peter Nüsser, Kleinmachnow (DE)

(73) Assignee: Berlin Heart GmbH, Berlin (DE)

( * ) Notice: Subject to any disclaimer, the term of this patent is extended or adjusted under 35 U.S.C. 154(b) by 0 days.

(21) Appl. No.: 15/367,914

(22) Filed: Dec. 2, 2016

(51) Int. Cl.
| | | |
|---|---|---|
| *A61M 1/12* | (2006.01) | |
| *A61M 1/10* | (2006.01) | |
| *A61M 25/09* | (2006.01) | |

(52) U.S. Cl.
CPC .......... *A61M 1/127* (2013.01); *A61M 1/1008* (2014.02); *A61M 1/1012* (2014.02); *A61M 1/125* (2014.02); *A61M 25/09* (2013.01)

(58) Field of Classification Search
CPC ...... A61M 1/127; A61M 1/125; A61M 25/09; A61M 1/1012; A61M 1/1008
See application file for complete search history.

(56) References Cited

U.S. PATENT DOCUMENTS

| | | | | |
|---|---|---|---|---|
| 6,136,025 | A * | 10/2000 | Barbut | A61F 2/90 604/530 |
| 6,981,942 | B2 * | 1/2006 | Khaw | A61M 1/101 600/16 |
| 8,012,079 | B2 | 9/2011 | Delgado, III | |
| 8,684,905 | B2 | 4/2014 | Jeevanandam et al. | |
| 2010/0210895 | A1 * | 8/2010 | Aboul-Hosn | A61M 1/101 600/16 |
| 2012/0041255 | A1 | 2/2012 | Delgado, III | |
| 2013/0138205 | A1 | 5/2013 | Kushwaha et al. | |
| 2013/0245361 | A1 * | 9/2013 | Wampler | A61M 1/101 600/16 |
| 2014/0171727 | A1 | 6/2014 | Nüsser et al. | |

FOREIGN PATENT DOCUMENTS

| | | |
|---|---|---|
| EP | 1789112 B1 | 9/2010 |
| EP | 2151257 B1 | 4/2013 |
| WO | 2014/179391 | * 11/2014 |

OTHER PUBLICATIONS

Mitamura, Yoshinori, "The Valvo-Pump—An Axial, Nonpulsatile Blood Pump", ASAIO Transactions 37, (1991), M510-M512.

* cited by examiner

*Primary Examiner* — Mark W Bockelman
(74) *Attorney, Agent, or Firm* — Schwegman Lundberg & Woessner, P.A.

(57) ABSTRACT

A disclosed apparatus or method can include or use a non-transluminally implantable blood pump housing, which can be sized and shaped to be implanted at an aortic valve of a human subject, the pump housing can include: a pump housing cross-sectional profile size that is larger than is passable via a blood vessel of the human subject; and a power connection, configured for being electrically connected to an intravascular lead that is sized and shaped to extend from the pump housing through a subclavian artery of the human subject.

30 Claims, 5 Drawing Sheets

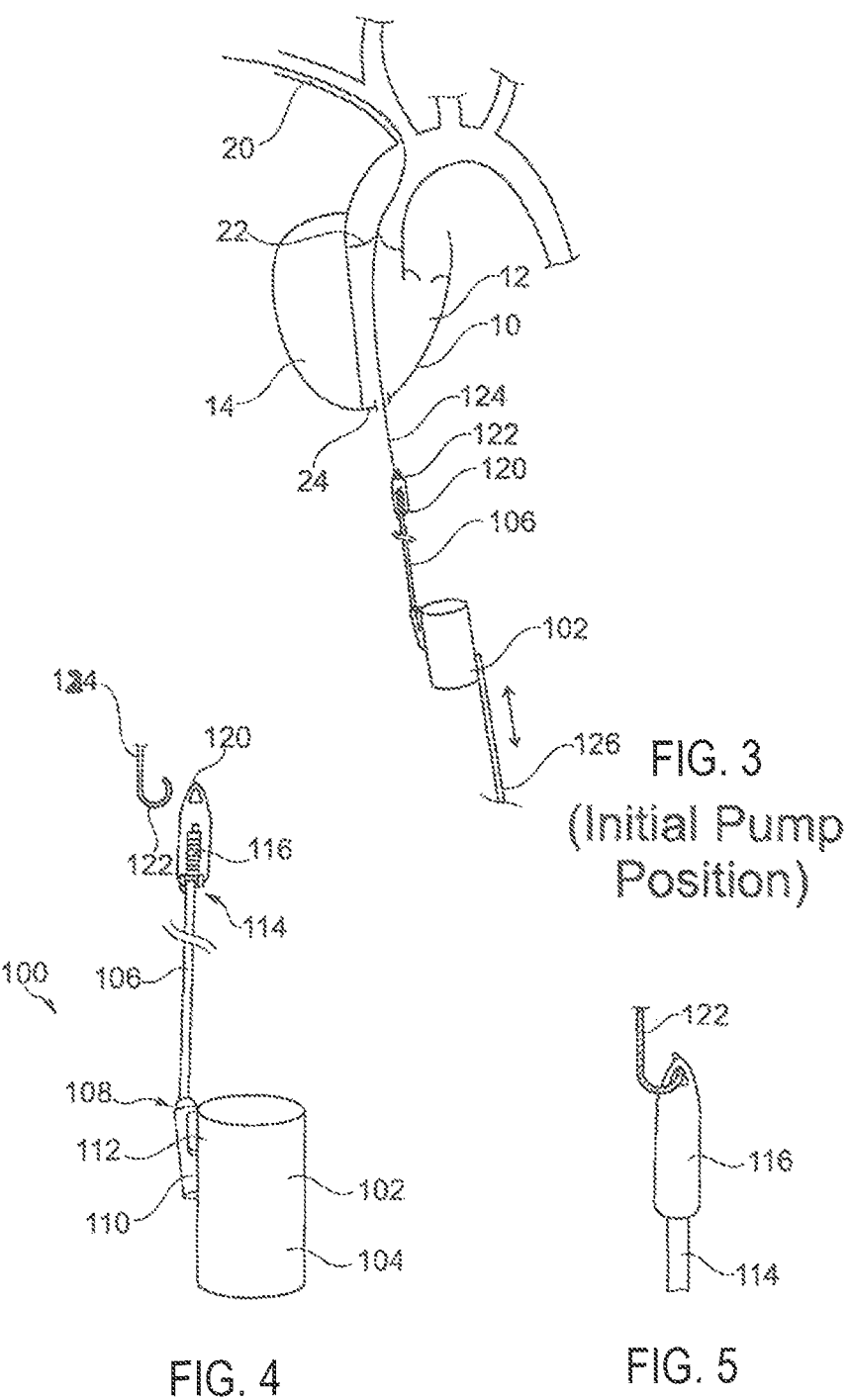

(Final Pump Position)

AORTIC PUMP DEVICES AND METHODS

TECHNICAL FIELD

This document relates generally to implantable heart pumps and ventricular assistance devices, and particularly, but not by way of limitation, to a non-transluminally implanted blood pump and power connection thereto, and associated methods of implantation and use.

BACKGROUND

Ventricular assistance devices include left ventricular (LV) pumps that can help the heart pump blood to the circulatory system, such as in a patient awaiting a heart transplant or such as to assist in treating cardiac insufficiency of patients of New York Heart Association (NYHA) Classes III to IV.

For example, Jeevanandam et al. U.S. Pat. No. 8,684,905 B2 relates to devices and methods for implanting, positioning, removing, replacing, and operating intra-aortic balloon pumps.

In another example, European Patent Number EP 1 789 112 B1 relates to an apparatus for long-term assisting a left ventricle to pump blood.

In a further example, European Patent Number EP 2 151 257 A1 relates to a method and apparatus for long-term assisting a left ventricle to pump blood, including a transluminally-deliverable support structure.

SUMMARY

The present inventors have recognized, among other things, that a problem to be solved is that transluminally-delivered implantable LV blood pumps are constrained by their size to dimensions that may not be capable of providing the desired amount of blood flow output from the pump. The present inventors have recognized that a non-transluminally-delivered LV blood pump, such as a transapically-delivered LV blood pump that can be placed in the ascending aorta, can be sized bigger, and therefore can be sized and otherwise be configured to be made capable of providing the desired amount of blood flow. Moreover, improved techniques of powering such a transapically-delivered LV blood pump can help advance their use and effectiveness.

This document describes, among other things, possible ways to have: a pump that can be located in the position of the aortic valve and a lead (e.g., a cable) that can be configured to communicate electricity, data, or both, such as via the subclavian artery, such as to a controller, a power source, or both, such as can be located within or outside of the body of the human subject.

Power and/or data may be brought into the body in a wireless manner, including when the power source and/or the controller are located within or outside of the body, such as using Transcutaneous Energy Transfer ("TET"), and data by using any suitable data protocol.

In an example, the lead/cable can be pulled into the subclavian artery, for example, as follows. First, a guidewire (e.g., a basic guidewire or even multiple guidewires, such as explained below) can be fed into the human subject's body (e.g., by Seldinger technique, such as explained below), and advanced into or even beyond the left ventricle (e.g., optionally exiting the left ventricle through a perforation of the left ventricle, such as at or near an apex of the left ventricle). Second, the pump and/or the lead can then be pulled into the heart. For example, the pump can be pulled into the region of the aortic valve. The lead can be pulled (e.g., by pulling the guidewire) through the subclavian artery, e.g., until it can be connected to a controller and/or a power source such as can be configured to control and/or power the pump. Third, any incisions of the body can then be closed and sealed.

Examples may include one or more of the following:

The pump may be pulled into its final position, e.g., at the heart valve, such as using the guidewire itself or using the lead that was previously pulled into the subclavian artery, e.g., using the guidewire;

A guiding tube or tunnel may be inserted into an incision of the apex, and through the left ventricle until the final position of the pump in the region of the aortic valve is reached; and The pump can be configured in a way that can always allow for a flow of blood through the pump, especially in case the pump does not work, in order to avoid a blockage of blood flow from the left ventricle into the aorta.

The pump can optionally be positioned in a very precise manner. In an embodiment, it is possible to removably attach a bar or a tube to the pump, such as can allow positioning of the pump through a puncture in the human body by the hand of the surgeon. Additionally or alternatively, a lead and/or a guidewire may optionally be removably fixed to the pump, such as to pull the pump in the direction of the aorta or the subclavian artery. By doing this, the pump can be positioned with utmost precision, as a force as well as a counterforce can be applied to the pump: one in the direction of the subclavian artery, one in the direction of the apex. After final positioning of the pump and/or fixation, preferably in the region of the aortic valve, the bar/tube that was used for positioning can be removed.

In this regard, it is also possible to provide a suitable lead for embodiments in which the lead is used to pull the pump. In these cases, it can be useful to have a lead that has one or more conductors/conductive wires such as for conducting data and/or electric current, and to have one or more extra wires that can be configured to provide additional or higher mechanical stability, such as when high stress/tension is applied to the lead, e.g., by pulling the lead in a direction of the aorta.

As explained herein, an aspect of the present subject matter can include placing a pump in a region of an aortic valve (which can be referred to as Transcatheter Aortic Pump Implantation ("TAPI"). In this regard, methods and devices used in Transcatheter Aortic Valve Implantation the ("TAVI") can be adapted for use in TAPI, such as adjustments that may be due to the nature of the pump instead of a valve. In the following "TAVI" is briefly explained.

TAVI involves inserting a new artificial heart valve inside the old tight valve, for instance, in conjunction with the use of a balloon catheter.

Briefly, there are several options for the insertion of a valve: (1) Transfemoral—through the femoral artery; or 2) Transapical—through a small cut on the left side of the apex of the heart.

In the context of the present document, transapical implantation of the pump can be focused, as the present inventors believe that an ordinary transluminal (e.g., transfemoral) implantation of the heart pump to be used may not be a preferred option.

The introduction of the lead and/or any other devices may be achieved using any suitable guidewire procedure, e.g., by using the Seldinger technique. In the context of the present document, Seldinger techniques entail percutaneous puncture, e.g., with a trocar or needle, tract or vessel dilation as needed, advancement of a guidewire and removal of the trocar. A lead can then be passed over the guidewire, such as to the destination of interest. After passing the lead, the guidewire can be withdrawn.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIGS. 1-10 show examples of a LV blood pump system.

DETAILED DESCRIPTION

Figure 1:
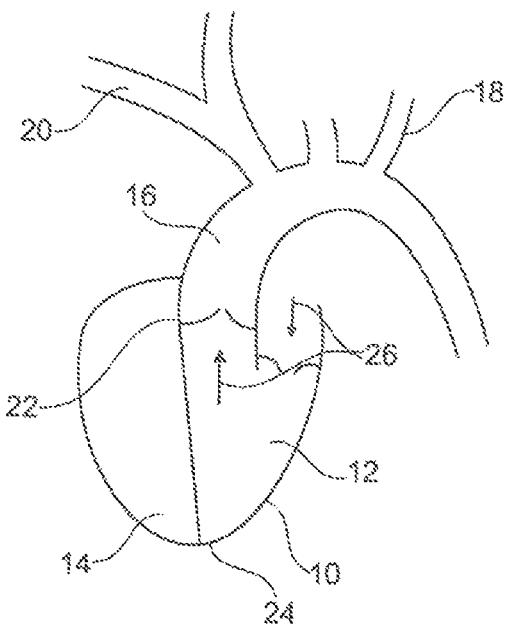

FIG. 1 shows a simplified schematic scheme of the human heart 10. The human heart has a left ventricle 12 as well as a right ventricle 14.

For the purpose of the present document, the blood flow as well as the blood vessels around the left ventricle are of particular interest. The arrows 26 show the flow of blood into the left ventricle and, through the aortic heart valve 22, out of the ventricle and into the aorta 16. Three branches are shown leaving the aorta in an upper direction. In the context of the present document, the subclavian arteries (left subclavian artery 18, right subclavian artery 20) are of particular interest. The guidewires/leads shown in this document are mostly guided through the right subclavian artery 20. Pumps are desired to be implanted in the region of the aortic valve 22, and preferably to be inserted through the apex 24 of the heart.

Figure 2:
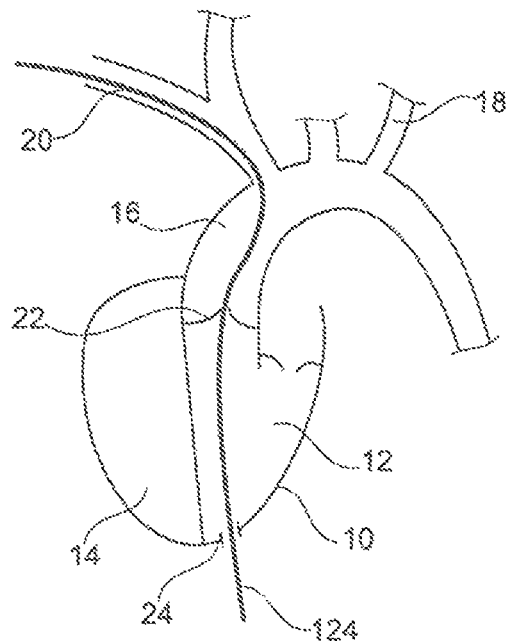
Figure 6:
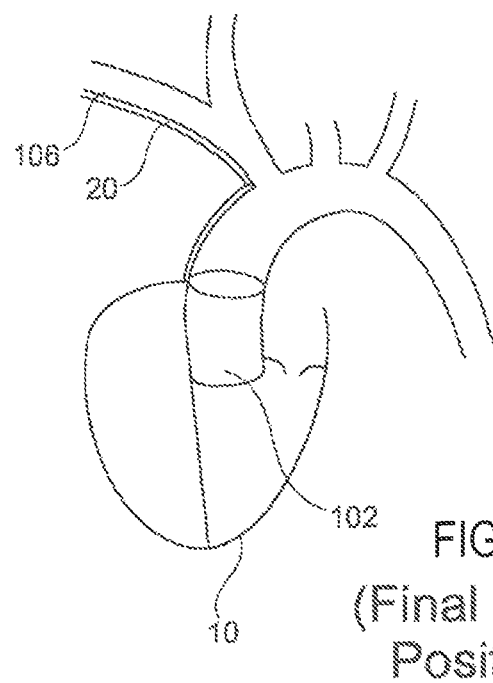

An example of this is shown in detail in FIG. 2. A guidewire 124 can, by using the so-called "Seldinger" technique, be brought into the right subclavian artery. The guidewire is led into the aorta 16, through aortic heart valve 22 and through a puncture of the heart in the region of the apex 24, as can be see in FIG. 2.

In the following, details of an example of a blood pump system as well as an example of a method are shown and described.

FIGS. 3, 4, 5, 6, (i.e., FIG. 3 "Initial Pump Position", FIG. 6 "Final Pump Position, FIG. 4 "Detail A", FIG. 5 "Detail B") shows an example including details of a LV blood pump system 100.

FIG. 3 "Initial Pump Position" shows an example of a state in which a pump 102 can be fixed to a bar or a tube-like structure 126, such as at or near its distal end. The bar 126 can include a handle, such as at or near its proximal end, that can be grasped by a surgeon and pushed through a puncture in the chest of a patient, such as to direct the pump 102 through a puncture in the region of the apex 24 and advanced into the region of the aortic valve 22. FIG. 3 "Initial Pump Position", FIG. 4 "Detail A", FIG. 5 "Detail B" show details and an example of a method of how to position and fix the pump 102 in the aortic valve region; this state can then be seen in FIG. 6 "Final Pump Position". When the pump 102 is finally positioned, the bar 126 can be disconnected from the pump 102 and removed, and the puncture in the apex 24 can be closed.

The blood pump 102 can be part of a blood pump system 100. The pump 102 can include an output pump housing 104. In an example, the pump housing 104 can carry a pump motor and a powered motorized impeller that can be located within the generally cylindrical or other pump housing 104. The pump motor can receive power or one or more control signals such as to drive the impeller to pump blood from a pump blood inlet to a pump blood outlet. For example, Nuesser et el. U.S. Patent Application Publication US 2014/0171727 A1 entitled BLOOD PUMP and/or U.S. Ser. No. 15/215,076, is incorporated by reference herein, including its description of an example of a blood pump including a housing, a pump motor, and an impeller, which can be modified and applied in the present context, such as described herein. For example, US 2014/0171727 discloses an axial pump with a radial outlet; for the purpose of the present document, a purely axial design can be an option, e.g., wherein inflow and outflow are arranged or aligned in the same direction.

In an example, the pump housing 104 can include a cross-sectional profile that is larger than is passable via a blood vessel of the human subject, but sized so that the blood pump 102 can be securely placed and located at the aortic valve or in the ascending aorta from an introductory location within the left ventricle, such as after having been introduced into the left ventricle via an incision in the left ventricle, such as at or near the apex of the left ventricle. Such transapical implantation of a the pump 102 can allow a larger cross-sectional dimension blood pump 102 to be located in the ascending aorta than would be allowed for a pump introduced transluminally into the ascending aorta from the other direction, that is, from an approach that is more distal from the heart than the ascending aorta, which would require passage of such a pump through a smaller blood vessel, such as the subclavian artery or even the aorta. The larger pump cross-sectional dimension of the blood pump 102, in turn, can be used to provide a more powerful blood pump 102 at the desired location within the ascending aorta, which can help provide better blood pumping through the circulatory system of the patient in which the pump 102 is implanted.

In the context of the present patent application, a blood pump 102 having a cross-sectional profile that is larger than 16 millimeters is defined as being larger than is passable via a blood vessel of the human subject (while still being capable of being placed and located at the aortic valve or in the ascending aorta), and smaller cross-sectional profiles are regarded as passable via a blood vessel of the human subject. In an example, the blood pump 102 can include an axial impeller that can be longitudinally arranged between a blood inlet and a blood outlet, such as to propel blood therebetween. The axial impeller can be sized, shaped, and otherwise configured to be capable of pumping at least 3 liters of blood per minute, which can be due, at least in part, to having a cross-sectional pump profile that is larger than 16 millimeters, which can allow a sufficiently larger axial impeller to produce such a rate of blood flow.

In a further example, the blood pump 102 cross sectional profile can be larger than 20 millimeters and can include an axial rotary impeller that can be longitudinally arranged between a blood inlet and a blood outlet, such that the impeller can be sized, shaped, and otherwise configured to be capable of pumping at least 3 liters of blood per minute.

In yet a further example, the blood pump 102 cross sectional profile can be larger than 25 millimeters and can include an axial impeller that can be longitudinally arranged between a blood inlet and a blood outlet, such that the axial impeller is sized, shaped, and otherwise configured to be capable of pumping at least 3 liters of blood per minute.

The pump system 100 can include an intravascular lead 106 or cable. A distal end 108 of the intravascular lead 106 can include a distal connector 110 that can be mechanically or electrically connected, or both, to a feedthrough connector 112 on the pump housing 104, such as at manufacturing, or such as after manufacturing, such as by a surgeon or other user. The feedthrough connector 112 can be located on a lateral generally cylindrical outer surface of the pump housing 104, or elsewhere, and can provide hermetically sealed connections to electrical components hermetically sealed within the pump housing 104. The feedthrough connector 112 can include a power connection, which can be configured for being electrically connected to an intravascular lead 106 that can be sized and shaped to extend from the pump housing 104 through an axillary or subclavian artery of the human subject into whom the pump 102 is implanted.

A proximal end 114 of the intravascular lead can include an external plug or other proximal connector 116. The proximal connector 116 can be mechanically or electrically connected, or both, to an external power or control unit 118. The external power or control unit 118 can be externally worn on the patient, placed near the patient or even internally within the patient (in this case, power may be supplied using "TET"—Transcutaneous Energy Transfer). The intravascular lead 106 can be long enough to extend from the implanted pump 102, such as when the pump 102 is located in the left ventricle or ascending aorta of the human patient, and to extend out through the axillary or subclavian artery to an percutaneous access point where it can exit and extend for direct or indirect connection to the external power or control unit 118 that can be worn by or placed near the patient or even internally within the patient, as explained elsewhere herein.

The intravascular lead 106 can include one or more separate electrically conductive wires or conductors extending for the length of the intravascular lead 106, such as between the proximal connector 116 and the distal connector 110. Such conductors can be configured to transmit electrical power to the blood pump 102, to communicate (individually, multiplexed, modulated, or otherwise) one or more control signals to the blood pump 102, or to communicate one or more sensor signals from the blood pump 102 to the external power or control unit 118. In case the lead itself is at least partially/temporarily used to pull the pump inside the heart, one or more additional wires for accommodating application of the mechanical stress/tension can be included, such as to avoid damage of the conductive wires/conductors.

The proximal connector 116 can include or can be integrated with a male or female or other towing engagement feature, for example, such as a proximal loop 120 that can be engaged by a corresponding reciprocal female or male or other towing feature, such as a hook 122 that can be located at the distal end of a separate intravascular thread or guidewire. A snap-connectors or one or more other engageable features can additionally or alternatively be used.

The embodiment of FIGS. 3, 4, 5, 6 showed the guidewire 124 and the lead 106 in series, e.g., such that when pulling the guidewire 124 in the direction of the blood flow, tension can be applied to the lead 106. For such applications, it can be desirable to have a lead 106 that can include an extra wire, such as to withstand high mechanical stress.

In the following, various embodiments are shown and described, such as in which most or all of the stress can be applied to the guidewire(s).

Figure 7:
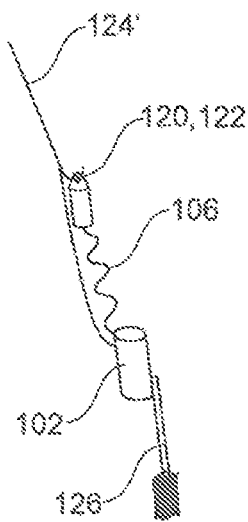
Figure 8:
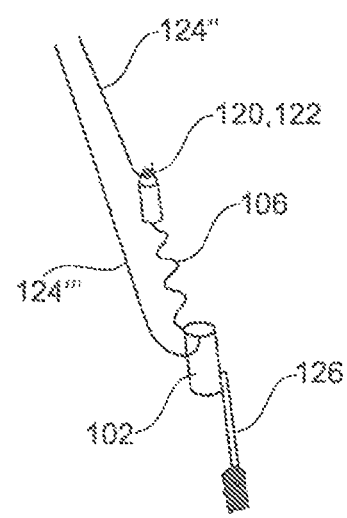

FIG. 7 shows an example of a single guidewire 124' such as with two hooks (a first hook 122 with its counterpart 120 (e.g., hook, eye, etc.) and a second hook that can engage the pump itself). The lead 106 is shown as limp and not under mechanical stress. The hook engaging the pump 102 can be disengaged, for example, as soon as the pump has reached its final position. In an embodiment, this disengagement (due to a mechanical coupling) can take place automatically, for example, as soon as the bar/tube-like structure 126 is removed from the pump 102.

In an embodiment, two guidewires can be provided. The guidewire 124" can be similar to the guidewire of FIGS. 3, 4, 5, 6. A second guidewire, shown as 124''', can engage the pump 102. As soon as the pump has reached its final position, the guidewire 124''' can be disengaged (e.g., automatically), such as with disengagement of the bar 126 from the pump, and can then be removed either through the apex or through the (right) subclavian artery. Using the guidewire 124", the lead 106 can be passed through the (right) subclavian artery and can then be fixed to a controller 118.

The blood pump housing 102 can optionally include an anchor or other support structure, such as to help secure the blood pump 102 at a desired location, such as at the aortic valve, or at a location in the ascending aorta. For example, a stent-like support structure can be attached to the blood pump housing 104, such as to help anchor it at a desired location by expanding the stent-like support structure, such as described in Delgado U.S. Pat. No. 8,012,079 entitled METHOD AND APPARATUS FOR LONG-TERM ASSISTING A LEFT VENTRICLE TO PUMP BLOOD, which is incorporated by reference herein, including its description of expanding a stent-like support structure to anchor a blood pump at a desired location, modified as appropriate for the present context.

In an example, the expandable support structure provided by the anchor can be made of Nitinol or other a shape-memory material and can be confined within a sleeve that can be attached to a trailing thread or line that can exit the heart at an incision in the LV apex through with the blood pump 102 was inserted. When the blood pump 102 has been placed at the desired location, the trailing thread or line can be tugged to pull the sleeve off the support structure and back out through the LV and the incision made therein, leaving the support structure unconfined and allowed to expand to keep the blood pump 102 anchored at the desired location.

Figure 9:
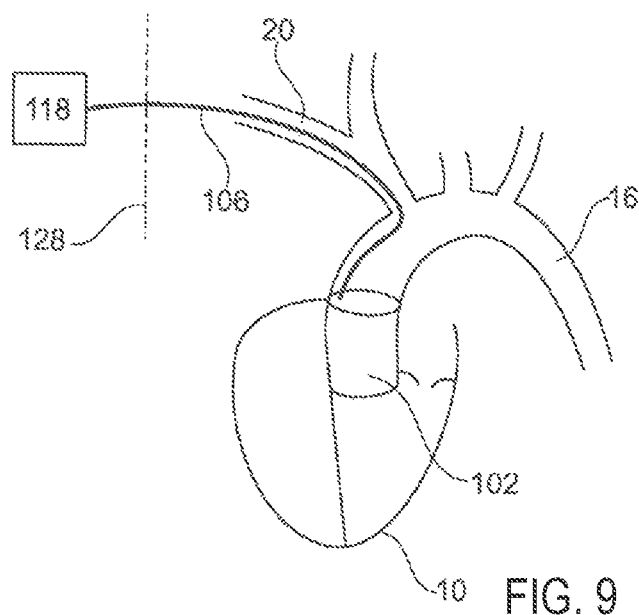
Figure 10:
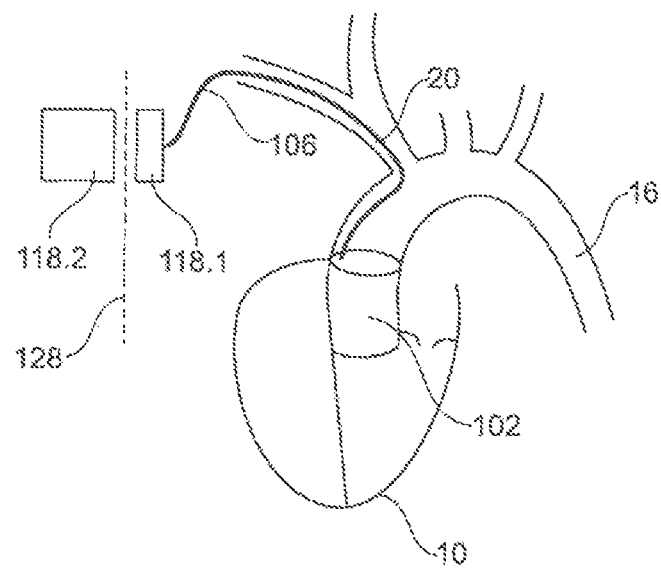

FIGS. 9 and 10 show examples of final states of the implantation of the pump 102 and its lead etc.

FIG. 9 shows an embodiment in which the pump 102 can be positioned in the aortic valve area, the lead 106 is passed through the right subclavian artery 20 and through the skin 128 of a patient to a controller 118, which can provides power, control data, or both.

In an embodiment such as shown in FIG. 10, the lead 106 can be fixed to a first part of the controller 118.1, which provides for control data and power. The part 118.1 of the controller can be located under the patient's skin 128. A second part of the controller, namely the part 118.2, can feed electrical energy through the skin 128 (such as using "TET", as explained above). Furthermore, (re-)programming of the device can also be performed in a wireless manner.

Figure 11:
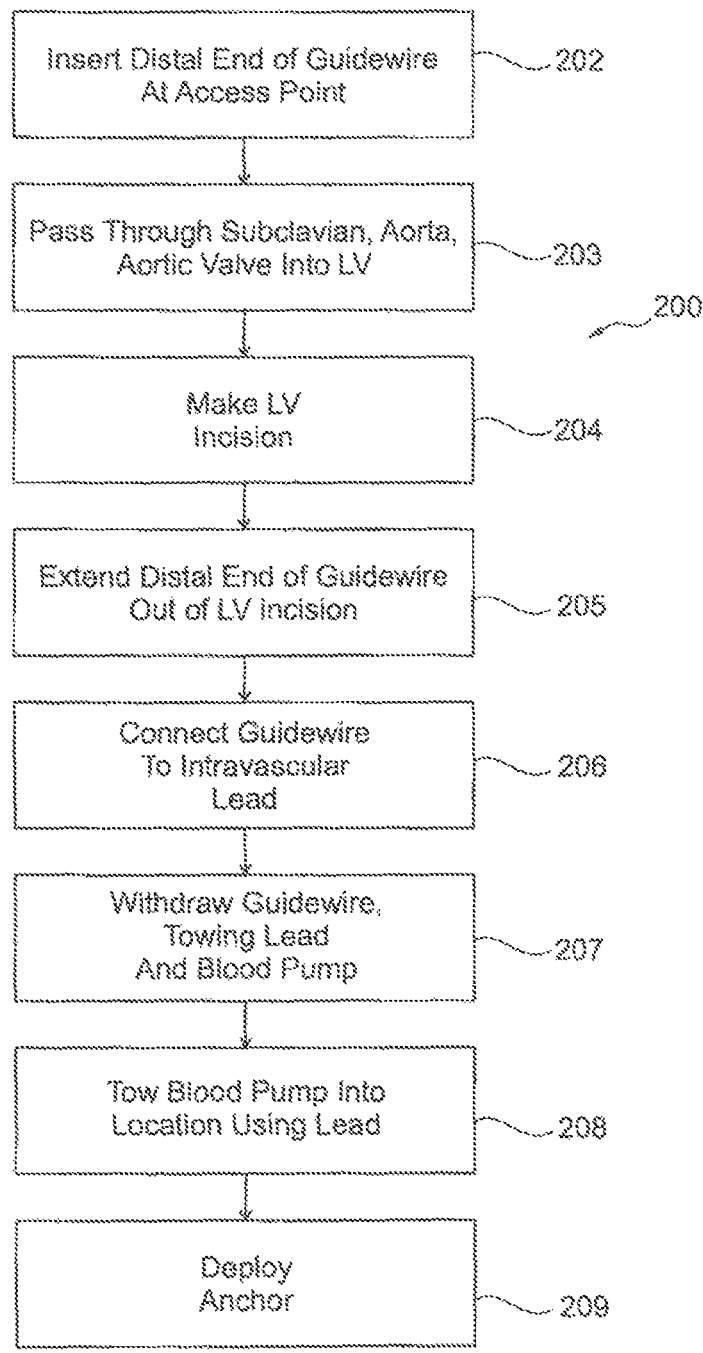
FIG. 11 shows examples of using the LV blood pump system of FIGS. 1-10.

FIG. 11 shows an example of a method 200 of using the blood pump system 100 of FIGS. 1-10. At 202, a distal end of the guidewire 134 can be inserted at a percutaneous access point to the subclavian artery, for example using the "Seldinger" technique.

At 203, the distal end of the guidewire can be transluminally and transvascularly passed through the subclavian artery, and through the aorta and the aortic valve, and into a left ventricle of the human subject.

At 204, an incision or other opening can be made into the left ventricle of the heart, such as at the LV apex. This can include open-heart surgery in which the sternum can be cracked to expose the heart, or it can include a laproscopic or other minimally-invasive procedure that allows sufficient access to the left ventricle of the heart to make a large enough incision to insert the blood pump 102 into the left ventricle.

At 205, the distal end of the guidewire 134 can be passed out of the LV to a location external to the heart.

At 206, a hook 122 or other towing feature of the distal end of the guidewire 134 can be attached to the loop 120 or other reciprocal towing feature on the proximal end of the intravascular lead 106 and/or the pump itself.

At 207, a proximal end of the guidewire 134, located externally of the percutaneous access point to the subclavian artery, can then by tugged by the user to withdraw the guidewire 134 through and from the subclavian artery while towing the intravascular lead 106 (and the blood pump 102 attached thereto) back through the LV, the aortic valve, the ascending aorta, and the subclavian artery to the percutaneous access point.

At 208, the proximal end of the intravascular lead 106 can then be used to further tow the blood pump 102 into a desired location, such as at the aortic valve or in the ascending aorta.

At 209, a stent or other anchor can be optionally deployed, such as to secure the blood pump 102 at the desired location at the aortic valve or in the ascending aorta. In an example, an expandable support structure provided by the anchor can optionally be confined within a sleeve that can be attached to a trailing thread or line that can exit the heart at an incision in the LV apex through with the blood pump 102 was inserted. When the blood pump 102 has been placed at the desired location, the trailing thread or line can be tugged to pull the sleeve off the support structure and back out through the LV and the incision made therein, leaving the support structure unconfined and allowed to expand to keep the blood pump 102 anchored at the desired location.

This approach to deploying the blood pump 102 transapically (rather than transvascularly or transluminally) through the LV and to a location at the aortic valve or within the ascending aorta, with an intravascular lead 106 providing power to the blood pump 102 can help reduce risks of thrombi formation that may otherwise be associated with passing the intravascular lead 106 through the left ventricle, such as out the transapical incision.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

REFERENCE NUMERALS 10 heart
12 left ventricle
14 right ventricle
16 aorta
18 left subclavian artery
20 right subclavian artery
22 aortic heart valve
24 apex
26 blood flow
100 blood pump system
102 blood pump
104 output pump housing
106 intravascular lead
108 distal end of intravascular lead 106
110 distal connector
112 feedthrough connector
114 proximal end of intravascular lead
116 proximal connector
118, 118.1, 118.2 external power or control unit
120 proximal loop
122 hook
124 guidewire
126 bar (or tube)
128 skin

What is claimed is:

1. A method comprising:
implanting a blood pump at an aortic valve or ascending aorta of a human subject, including transapically introducing the blood pump into a left ventricle of the heart of the human subject;
passing a guidewire from a percutaneous access point through a subclavian artery of the human subject, through an aorta of the human subject, and into or through a left ventricle of the human subject;
passing an intravascular lead, connected to the blood pump, through a subclavian artery of the human subject to receive power at the blood pump via the intravascular lead;
connecting the guidewire to the intravascular lead in the left ventricle of the human subject or external to the heart or external to the human subject; and
towing the blood pump, using the intravascular lead, into a location at the aortic valve or ascending aorta of the human subject.

2. The method of claim 1, comprising connecting the blood pump to the intravascular lead before the blood pump is in the left ventricle of the heart of the human subject and before the blood pump is further introduced into the location at the aortic valve or ascending aorta of the human subject.

3. The method of claim 2, wherein passing the intravascular lead through the subclavian artery of the human subject includes towing the blood pump into, from, or through the apex or other location of the left ventricle of the heart of the human subject into the ascending aorta of the human subject.

4. The method of claim 1, comprising pulling the intravascular lead from the left ventricle through the subclavian artery of the human subject via a guide wire extended the opposite direction from a percutaneous access point for the subclavian artery.

5. The method of claim 1, wherein passing the intravascular lead through the subclavian artery of the human subject is performed concurrently or after introducing the blood pump into the left ventricle of the heart of the human subject.

6. The method of claim 1, wherein passing the intravascular lead through the subclavian artery of the human subject is performed while further introducing the blood pump into the location at the aortic valve of the subject.

7. The method of claim 6, comprising anchoring the blood pump at an aortic valve or ascending aorta of the subject.

8. The method of claim 7, wherein passing the intravascular lead through the subclavian artery of the human subject is performed before anchoring the blood pump at the aortic valve or ascending aorta of the subject.

9. The method of claim 7, wherein the anchoring the blood pump at the aortic valve or ascending aorta of the subject includes expanding the anchor to secure the blood pump at the aortic valve or ascending aorta of the subject.

10. The method of claim 1, comprising:
carrying at least a portion of the intravascular lead with or attached to the blood pump while the blood pump is being introduced from the left ventricle of the heart of the human subject into the ascending aorta of the human subject.

11. The method of claim 1, wherein implanting a blood pump comprises using a blood pump having a pump housing cross-sectional profile size that is larger than is passable via a blood vessel of the human subject.

12. The method of claim 1, wherein implanting a blood pump comprises using a blood pump wherein the blood pump cross sectional profile is larger than 16 millimeters, and wherein the blood pump includes an axial impeller that is longitudinally arranged between a blood inlet and a blood outlet, whereby the axial impeller is sized, shaped, and otherwise configured to be capable of pumping at least 3 liters of blood per minute.

13. The method of claim 1, wherein implanting a blood pump comprises using a blood pump wherein the blood pump cross sectional profile is larger than 20 millimeters and includes an axial impeller that is longitudinally arranged between a blood inlet and a blood outlet, whereby the axial impeller is sized, shaped, and otherwise configured to be capable of pumping at least 3 liters of blood per minute.

14. The method of claim 1, wherein implanting a blood pump comprises using a blood pump wherein the blood pump cross sectional profile is larger than 25 millimeters and includes an axial impeller that is longitudinally arranged between a blood inlet and a blood outlet, whereby the axial impeller is sized, shaped, and otherwise configured to be capable of pumping at least 3 liters of blood per minute.

15. The method of claim 1, comprising using the intravascular lead that is sized and shaped to extend from the pump housing, when located at the aortic valve or the ascending aorta, through the subclavian artery of the human subject to exit from the human subject.

16. A method comprising:
implanting a blood pump at an aortic valve or ascending aorta of a human subject, including transapically introducing the blood pump into a left ventricle of the heart of the human subject;
passing a guidewire or intravascular lead between a percutaneous access point and through a subclavian artery of the human subject, through an aorta of the human subject, and into or through a left ventricle of the human subject; and
towing the blood pump, using the guidewire or the intravascular lead, into a location at the aortic valve or ascending aorta of the human subject.

17. The method of claim 16, wherein passing a guidewire or intravascular lead comprises passing a guidewire from a percutaneous access point through a subclavian artery of the human subject, through an aorta of the human subject, and into or through a left ventricle of the human subject.

18. The method of claim 16, comprising passing an intravascular lead, connected to the blood pump, through a subclavian artery of the human subject to receive power at the blood pump via the intravascular lead.

19. The method of claim 16, comprising connecting the guidewire to the intravascular lead in the left ventricle of the human subject or external to the heart or external to the human subject.

20. The method of claim 16, comprising connecting the blood pump to the intravascular lead before the blood pump is in the left ventricle of the heart of the human subject and before the blood pump is further introduced into the location at the aortic valve or ascending aorta of the human subject.

21. The method of claim 20, wherein passing the guidewire or intravascular lead through the subclavian artery of the human subject includes towing the blood pump into, from, or through the apex or other location of the left ventricle of the heart of the human subject into the ascending aorta of the human subject.

22. The method of claim 16, comprising pulling the intravascular lead from the left ventricle through the subclavian artery of the human subject via a guidewire extended the opposite direction from a percutaneous access point for the subclavian artery.

23. The method of claim 16, wherein passing the guidewire or intravascular lead through the subclavian artery of the human subject is performed concurrently or after introducing the blood pump into the left ventricle of the heart of the human subject.

24. The method of claim 16, wherein passing the guidewire or intravascular lead through the subclavian artery of the human subject is performed while further introducing the blood pump into the location at the aortic valve of the subject.

25. The method of claim 16, comprising anchoring the blood pump at an aortic valve or ascending aorta of the subject.

26. The method of claim 25, wherein passing the intravascular lead through the subclavian artery of the human subject is performed before anchoring the blood pump at the aortic valve or ascending aorta of the subject.

27. The method of claim 25, wherein the anchoring the blood pump at the aortic valve or ascending aorta of the subject includes expanding the anchor to secure the blood pump at the aortic valve or ascending aorta of the subject.

28. The method of claim 16, comprising:
carrying at least a portion of the guidewire or intravascular lead with or attached to the blood pump while the blood pump is being introduced from the left ventricle of the heart of the human subject into the ascending aorta of the human subject.

29. The method of claim 16, wherein implanting a blood pump comprises using a blood pump having a pump housing cross-sectional profile size that is larger than is passable via a blood vessel of the human subject.

30. The method of claim 16, wherein implanting a blood pump comprises using a blood pump wherein the blood pump cross sectional profile is larger than 16 millimeters, and wherein the blood pump includes an axial impeller that is longitudinally arranged between a blood inlet and a blood outlet, whereby the axial impeller is sized, shaped, and otherwise configured to be capable of pumping at least 3 liters of blood per minute.

* * * * *